United States Patent [19]
Mathewson

[11] Patent Number: 5,785,980
[45] Date of Patent: Jul. 28, 1998

[54] WATER HYDRATABLE GEL-FILLED TUBULAR MATERIAL ENVELOPE

[76] Inventor: Paul R. Mathewson, 7726 N. Buckboard Dr., Park City, Utah 84098

[21] Appl. No.: 789,468

[22] Filed: Jan. 27, 1997

Related U.S. Application Data

[63] Continuation-in-part of Ser. No. 492,398, Jun. 19, 1995, Pat. No. 5,597,577.
[51] Int. Cl.$^6$ .............................. A61F 7/00; A61F 7/02; A61F 7/10; A61F 7/12
[52] U.S. Cl. .................. 424/402; 62/529; 62/530; 128/402
[58] Field of Search .............................. 424/402; 62/529, 62/530; 128/402

[56] References Cited

U.S. PATENT DOCUMENTS

| | | |
|---|---|---|
| 3,545,230 | 12/1970 | Morse . |
| 4,055,188 | 10/1977 | Pelton ................................. 128/402 |
| 4,910,978 | 3/1990 | Gordon et al. ....................... 62/530 |

*Primary Examiner*—Thurman K. Page
*Assistant Examiner*—Sharon Howard
*Attorney, Agent, or Firm*—Trask, Britt & Rossa

[57] ABSTRACT

A device for providing cooling relief for the body, especially during physical recreational/leisure activities, is disclosed which makes use of a water-permeable tubular material envelope containing a particulate resinous gel-forming material. The particulate resinous material, when hydrated by emersion in water, forms a soft pliable gel-like substance. The cooling effect of this device is provided by the evaporation of water from the surface of the material envelope. The filamentous components of the material envelope, by capillary action, wick water from the interstitial spaces in the water hydrated gel material, carrying the water to the material/air/skin interface. The water evaporating from that interface results in the evaporative cooling effect. In an alternative embodiment, the device also includes means for producing either an endothermic or exothermic reaction within or in close proximity to the material envelope for the purpose of enhancing the cooling process (endothermic), particularly in higher humidity conditions, or, alternatively, to provide a source of heat (exothermic) in certain situations, for example, for application to sore muscles. The device is simple and convenient to use in virtually any location, indoors or out, and can be utilized in the cooling configuration during a variety of recreational and leisure activities to mitigate the uncomfortable effects of heat.

10 Claims, 2 Drawing Sheets

WATER HYDRATABLE GEL-FILLED TUBULAR MATERIAL ENVELOPE

This is a continuation-in-part application of prior U.S. application Ser. No. 08/492,398 filed Jun. 19, 1995, now U.S. Pat. No. 5,597,577.

BACKGROUND OF THE INVENTION

1. Field of the Invention

This invention relates to devices for cooling the body. Outdoor activities, particularly those participated in during the hotter times of the year, may lead to overheating, fatigue, excessive perspiring, and other related discomforts. It is known that application of water, cool compresses or other such cooling devices can relieve many of the symptoms related to overheating and help to prevent more serious consequences such as heat stroke. The present invention addresses such concerns related to, or caused by, outdoor recreational or other leisure activities during warm weather where overheating is often of concern.

2. State of the Art

All prior art in this particular field consists of relatively simple "home" remedies, the majority of which involve wrapping a moist piece of cloth, such as a towel, around the head or neck. While this approach may be moderately effective initially, the cooling effect is short-lived due to the rapid evaporation of the moisture from the towel or cloth.

Other cooling devices have been patented, all of which have been directed to therapeutic use using ice, and/or gels of various sorts which require freezing. Such devices are directed to the therapeutic cooling of certain body parts which have been injured in some way and require that the afflicted area be cooled to a significant degree. Therapeutic cooling requires that the temperature of the afflicted body area be significantly dropped (from about 35° C. to about 5° C.) for a period of at least fifteen minutes. This cooling usually relies on the high latent heat of fusion of water. "Latent heat of fusion" refers to the relatively large amount of heat required to melt ice. This results in the ability of the cooling device containing the frozen water (ice) to provide a relatively cold environment for a length of time sufficient to drop the temperature of the body part to the required extent to achieve therapeutic benefit. Such devices are disclosed in U.S. Pat. Nos. 3,545,230; 4,671,267, and 4,910,978.

Therapeutic cooling devices rely on the heat of fusion of water, in the form of ice, to provide the necessary cooling effect. Prior art discloses a number of configurations taking advantage of this property of water. One common feature of such devices is that they are comprised of relatively non-permeable plastic or other vinyl-like envelopes containing, water or a water-containing gel-like material. In some inventions, the envelope consists of a plastic/vinyl envelope which is laminated to an outer material constructed from a woven or non-woven material. In any case, this envelope is essentially non-permeable to the free flow of water from inside the envelope to the outside.

The reliance of these therapeutic devices on the heat of fusion of water, that is the high heat capacity of the frozen water as ice, as well as the non-permeable nature of the container in which the water and/or gel is found, makes them unsuitable for the kind of recreational purpose for which the present invention is designed. The therapeutic devices must be exposed to very cold temperatures (below freezing) prior to use, in order to lower the temperature of the water/gel sufficiently to provide a therapeutic benefit when used by the patient. Once exposed to the very warm conditions experienced in warm weather outdoor activities, the cooling effect would rapidly dissipate and could not be regenerated without returning the device to a refrigerator/freezer.

While several inventions have been patented disclosing methods for achieving a therapeutically significant drop in temperature at a specific location of an injury on the human body, these devices can be used only under restricted conditions and are wholly unsuited for cooling the body under conditions experienced while engaged in any of the many activities practiced out of doors in warm weather. Thus, a need exists for a simple, convenient device which can provide a sense of cooling relief to the wearer while engaged in any of the myriad forms of outdoor or indoor recreation.

SUMMARY

The present invention provides a greatly improved means of providing cooling relief from the thermal effects of hot weather or physical activity which does not depend on the conventional means of heat of fusion of water. The detrimental results arising from exposure to the heat of the sun and of physical exertion during vigorous activities can be serious. The present invention diminishes such thermal effects by providing a mechanism through which the body may be cooled by evaporative cooling during such exposure.

The invention generally includes a tubular material wrap which can be applied to various areas of the body which are sensitive to heat and cold. These areas include, but are not restricted to, the neck, head, face, wrists, shoulders, feet and back among others. The tubular material wrap embodied in this invention comprises a water-permeable material envelope comprised from natural or synthetic, woven or non-woven material which has the capability of transporting fluid therethrough. The material envelope is sized to contain a measured portion of an evaporative cooling agent, such as a particulate gel-forming resinous material. The resinous material is capable of forming a gel when exposed to water. The dry resinous gel-forming material is capable of absorbing several hundred times its dry weight in water. The particulate resinous gel-forming material is contained within the water-permeable tubular material wrap and is hydrated by contacting said material wrap containing the particulate resinous gel-forming material with sufficient water. The non-hydrated resinous gel-forming material may have a particle size from about 5 microns to about 10,000 microns, the preferred size being in the range of about 200 to 2,000 microns.

The water-permeable material wrap containing the hydrated and swollen resinous gel-forming material allows for the evaporation of water from its surface. The water slowly migrates from the internal interstices of the hydrated gel material to the surface of the material wrap, where it evaporates. It is this evaporation of water, rather than the melting of frozen water (ice), which provides the cooling effect through the phenomenon referred to as evaporative cooling. While it may be desirable to place the material wrap containing the hydrated gel-forming material in a refrigerator to provide for additional cooling effect, cooling can and will be felt without prior refrigeration due solely to the evaporative cooling effect. Thus, while hydrated, the device can be used at virtually any location, outdoors or indoors, with consequent cooling effect. Moisture will be lost due to evaporation over time. Rejuvenation of the device can be accomplished simply by exposing the device to any source of water. If the device is allowed to dehydrate completely, the device returns to its original size, shape and weight, which is significantly less in all respects compared to the hydrated form. Thus, the dehydrated device can be conveniently stored and transported when not in use.

The water-permeable material wrap containing the resinous gel-forming material is constructed in such a way as to produce air channels positioned between the external surface of the material wrap and the part of the body immediately adjacent to the material wrap. These air channels are designed as integral aspects of the construction of the device and are meant to provide a space through which air can move while the material wrap is worn. The air channels provide for increased air movement between the external surface of the tubular material wrap and the skin. This increased air movement encourages additional evaporation of water from the surface of the material wrap, thus enhancing the cooling effect.

In the first embodiment of the invention, the evaporative cooling agent retained within the envelope of the water-permeable material wrap is a dry resinous gel-forming material which becomes hydrated and swollen upon contact with water. In an alternative embodiment, the evaporative cooling agent also comprises a quantity of a reactable material having a relatively high solubility and heat of solution ($\Delta H$), and a source of fluid reactant, such as water, located within an envelope and positioned to surround the quantity of reactable material. Alternatively, the reactable material can be positioned in such a way that it may surround or lie in close proximity to a contained reservoir of fluid reactant. The quantity of reactable material and source of fluid reactant may be positioned adjacent to the tubular material wrap containing the gel-forming resinous material. The quantity of reactable material is preferably a compound, such as ammonium nitrate, silver nitrate, potassium nitrate, or the like, which, when contacted with a fluid reactant, such as water, produces an endothermic reaction, thereby increasing the cooling effect of the device. The latter embodiment is particularly useful under conditions of higher humidity which may tend to lessen the effectiveness of the evaporative cooling alone.

In addition, a further embodiment of this invention may provide a heating effect through the use of an exothermic reaction as opposed to the endothermic reaction described in the previous embodiment. The physical arrangement could be the same as described previously for the endothermic reaction. In this instance, a reactable material, such as calcium chloride, potassium hydroxide or the like, which, when contacted with a fluid reactant, such as water, produces an exothermic reaction, releases heat to the immediate surroundings. This reaction may allow the same invention a dual purpose in terms of being useful for the application of heat, for example, to a sore muscle of the body.

DETAILED DESCRIPTION OF THE ILLUSTRATED EMBODIMENT

The present invention provides, in a simple and convenient form, the means of furnishing cooling relief to the body during the pursuit of recreational activities. The present device is best suited to application to the forehead or the back of the neck, although other configurations could apply to virtually any body location.

As shown in the accompanying drawings, this cooling compress comprises a material holder 10, adapted to fit against the appropriate body part of the individual wearer, in which an amount of dry particulate gel-forming resinous material 11 is held. In the unhydrated form, the material holder 10, as assembled, is in the form of a flat, lightweight material envelope 12. When the entire material envelope 12 is immersed in water, the particulate gel-forming material 11 absorbs several hundred times its own weight in water and expands to fill the inner volume of the material envelope 12.

Figure 1:
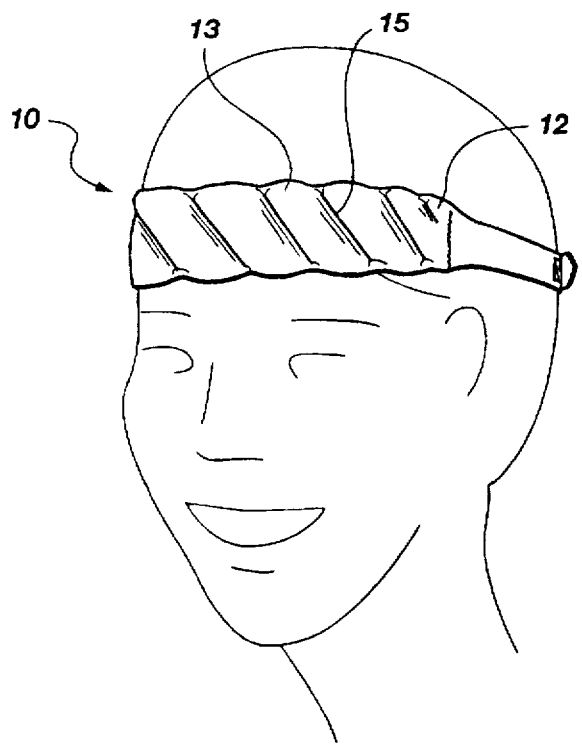
FIG. 1 is a front view illustrating the present invention in its likely use orientation across the forehead of the user.

FIG. 1 illustrates the material wrap or holder 10 as it might be worn when in use. While exemplar embodiments of the present invention are herein illustrated and described, it is not intended to limit the invention to the illustrated embodiments. Additional embodiments and configurations may also be made which provide for use of the device for additional purposes and to other areas of the body. The present device may be constructed from any type of fabric material meeting the stated requirements such as a cotton material, but could be constructed from any material suitable for the purpose.

Figure 3:
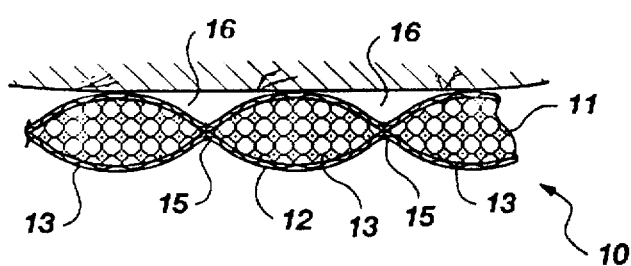
FIG. 3 is a transverse sectional view of the assembled, hydrated material wrap in contact with the skin of the forehead or other body part, in which the hydrated gel segments are shown as well as the air channels.
Figure 2:
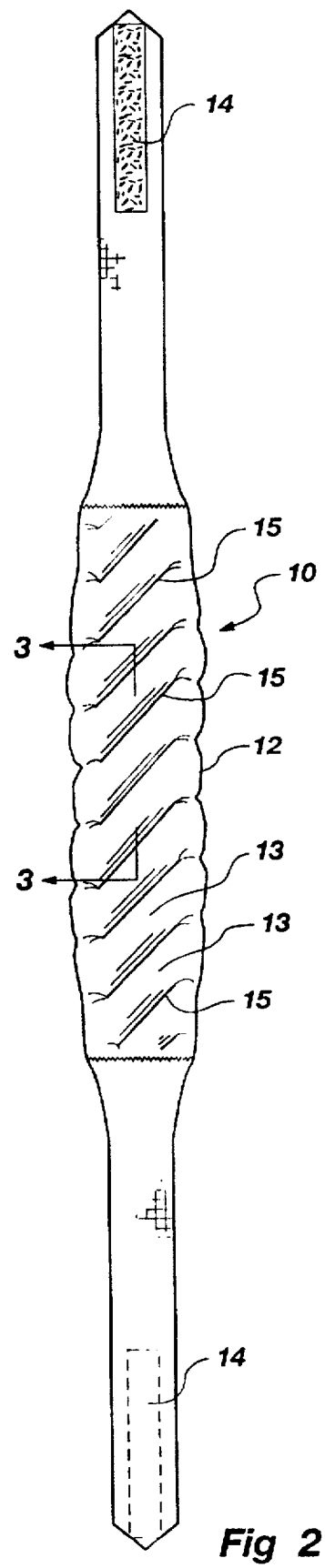
FIG. 2 is a top view of the invention showing its general shape and construction. This view illustrates the assembled, hydrated device and the lateral seams sewn across the long axis of the tubular material section, forming gel-filled segments.

FIG. 2 shows the assembled, hydrated material wrap or holder 10. As shown, the invention consists of a tubular section of appropriate material forming a lightweight envelope 12. Lateral seams 15 are shown across the long axis of this envelope 12 which form the segments 13 which are filled with the gel-forming resinous material 11 (FIG. 3). The device is shown using Velcro closures 14 to secure the invention in place. The device may also be tied or snapped to secure it in place. Alternatively, the device may be formed as a collar of material having no ends, but having sufficient elasticity to be positionable over or about a part of the body. In a further alternative, the device may be configured to fit within an appropriately sized pocket which may be built into an item of apparel in the desired location to contain the invention. That is, for example, a pocket formed in the collar of a garment may be sized to receive the device so that cooling may be delivered to the neck of the wearer.

In normal use, the present invention is used in the hydrated condition. This hydration may be accomplished by immersing the entire material envelope 12 in water and allowing the particulate resinous material to absorb water. The time required to absorb sufficient water depends both on the particle size of the resinous material 11 as well as the temperature of the water. The hydration time is inversely proportional to the water temperature and directly proportional to the particle size. The material envelope 12 is permeable to water and so does not restrict the flow of water into the inner volume of the envelope 12 where the particulate resinous material 11 is located. The material envelope 12 then maintains a wicking action which slowly draws water out from the interstices of the gel-forming material 11 and delivers the water to the surface of the material envelope 12. The water at the envelope/air interface will then evaporate, providing a cooling effect over an extended period of time through evaporative cooling.

Several alternatives exist in so far as the construction of this device is concerned. As mentioned, in filling the material envelope with an amount of particulate resinous gel-forming material 11, the gel-forming material 11 may be either in the dry, unhydrated form, or, alternatively, can be, hydrated prior to addition to the material envelope 12.

In using a continuous slab of resinous gel-forming material, the hydrated gel-forming material could be cut to the appropriate size and shape and the envelope material sewn around it to form the completed envelope 12. Alternatively, it is also possible to sew the envelope around an appropriately sized piece of dry, unhydrated resinous gel-forming material 11.

Resinous gel-forming material which may be of use in the present invention can be prepared from a variety of starting materials including, but not restricted to:

Polyacrylamide
Anionic polyacrylamide
Polyvinyl alcohol
Maleic anhydride—vinylether copolymers
Poly(ethylene oxide)
Polyacrylic acid
Ethylene-maleic anhydride copolymers
Polyvinylether
Dextran
Polymethacrylic acid
Polyvinylsulfonic acid
Polystyrene sulfonic acid
Polyvinylamine The present invention is not limited to the use of the starting materials listed here, but may include copolymers of one or more of either the materials mentioned, or other materials similar to these and suitable for forming a hydratable gel-like material. The preferred embodiment of the present invention is comprised from a group consisting of polymers, copolymers and terpolymers containing acrylic acid or acrylamide monomer moieties and, most preferably, a polymer of acrylamide.

The mechanism by which the present invention provides the cooling relief is primarily through evaporative cooling. Water from the interstices of the hydrated gel-forming material 11 is wicked to the surface of the material envelope 12 through the capillary action of the individual material fibers. The moisture thus wicked to the surface evaporates and results in a cooling sensation against the skin. While the degree of cooling is not suitable for therapeutic applications, it is effective in cooling the body during physical exertion accompanying recreational/leisure outdoor/indoor activities.

As shown in FIG. 3, the material envelope 12 can be constructed in such a way as to further enhance the cooling effect of the evaporation of water. The material envelope 12 consists of a tubular section containing the resinous gel-forming material 11. Lateral seams 15 may be sewn into the material envelope 12 as shown, which are generally perpendicular to, or at an angle to, the long axis of the material envelope 12. When the gel-forming material 11 is hydrated, the material envelope 12 is transformed from a flat configuration to one which is comprised of numerous gel-filled segments 13. Each segment 13 is approximately cylindrical in shape, having a semi-spherical section which remains in contact with the skin during use. Each gel-filled segment 13 is separated by a cleavage which provides an air channel 16 between the material envelope and the skin. This channel 16 allows for the transport of air between the material envelope 12 and the skin of the wearer. FIG. 3 illustrates the construction of the gel-filled segments 13 and their orientation to the skin when in the hydrated form. Also illustrated are the air channels 16 formed between the surface of the invention and the skin of the user of the device. The increased air flow thus achieved promotes additional evaporation of water at the air/material envelope interface, thus enhancing the evaporative cooling effect.

FIG. 3 illustrates one embodiment of the invention comprising a tubular material envelope 12 having a plurality of segmented sections 13, a substantial portion of the interior volume of the segments being filled with a gel-forming resinous material 11. The resinous gel-forming material 11 is capable of absorbing considerable quantities of water, the water then being slowly released from the hydrated gel-forming material 11 and traveling to the exterior surface of the material envelope 12 from which it evaporates. The resulting evaporative cooling provides the primary basis for the perceived cooling effect. An alternative embodiment of the present invention is shown in FIG. 4.

Figure 4:
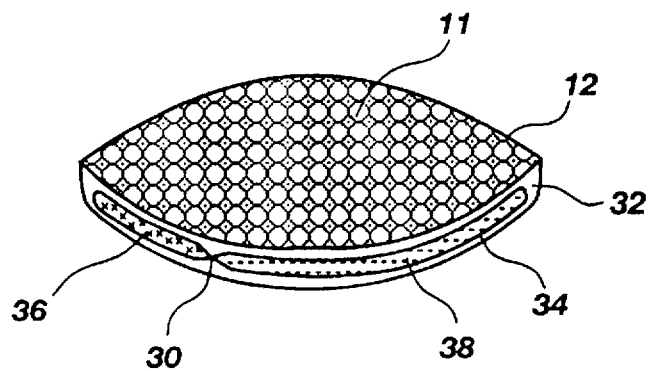
FIG. 4 is a view in cross section taken through the short axis of the envelope of an alternate embodiment constructed with a pocket containing a supplemental source of cooling or heating.

FIG. 4 is a view in cross section of the material envelope 12 taken through the short axis thereof. In this embodiment, a pocket 32 may be constructed which extends along the length of the tubular material envelope 12 and is coextensive with it. Within this pocket is a removable, continuous, non-porous enclosure 34 containing both a reactant material 36 and a fluid reactant 38. Either, or both, the reactant material 36 and the fluid reactant 38 are compartmentized, for example, by use of a heat seal 30, within the non-porous enclosure 34, precluding the premature combination of the reactant material 36 with the fluid reactant 38. The non-porous enclosure 34 is structured to prevent any mixture between the fluid reactant/chemical compound and the surrounding gel-forming resinous material 11. At the desired time, the compartment containing either the reactant material 36 and/or the fluid reactant 38 may be ruptured, for example, by breaking of the heat seal 30, resulting in the admixing of the reactant material 36 with the fluid reactant 38. As one alternative, the reactant material may be a compound such as ammonium nitrate, silver nitrate, potassium nitrate, or the like, which, when contacted with a fluid reactant, such as water, produces an endothermic reaction, thereby increasing the cooling effect of the device. In another embodiment, the reactant material may be a compound such as calcium chloride, potassium hydroxide or the like, which, when contacted with a fluid reactant, such as water, produces an exothermic reaction. In this case, the result of the reaction would be the release of heat to the immediate surroundings.

Figure 5:
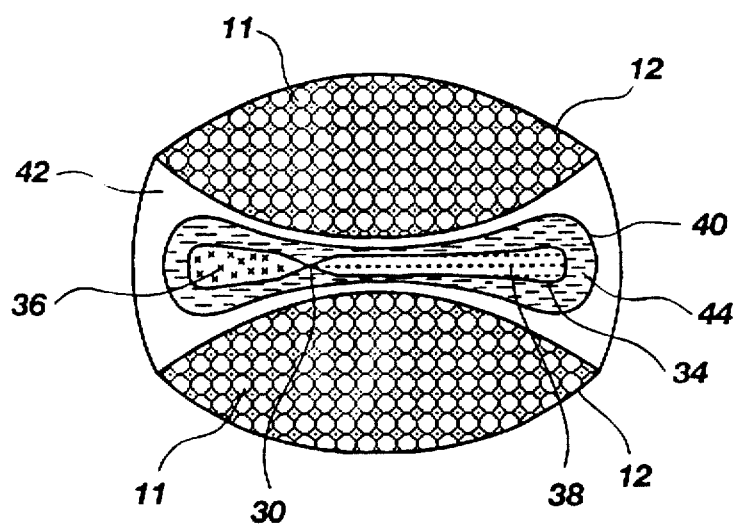
FIG. 5 is a view in cross section taken through the short axis of the envelope of an alternate embodiment showing the conjoining of two material envelopes with an interior space containing a supplemental source of cooling or heating.

FIG. 5 illustrates yet another alternative embodiment of the present invention in which two such material envelopes have been conjoined, forming an interior space 42. Within said interior space 42 may be positioned an elongated enclosure 40 comprising a porous flexible membrane material such as cellulose acetate which allows for the slow release of water from its interior space to its exterior. Within said porous elongate enclosure 40 may be positioned an assembly similar to that described in the previous embodiment comprising a non-porous enclosure 34, itself containing a reactant material 36 and a fluid reactant 38 as described in the previous embodiment. Within the first porous enclosure 40, but outside the inner non-porous enclosure 34, may be a quantity of water 44. As described in the previous embodiment, a barrier between the fluid reactant 38 and the reactant material 36 may be ruptured, allowing for the admixing of fluid reactant 38 and reactant material 36. This reaction, whether endothermic or exothermic will result in the transfer of thermal energy (either cool or heat) to the surrounding quantity of water 44. This cooled or heated water may then slowly suffuse from the interior space of the porous enclosure 40 to the exterior space and migrate into the surrounding material envelope 12, being absorbed by the gel-forming resinous material 11. Thus, in the case of an endothermic reaction, the cooled water within the porous enclosure 40 will migrate to the gel-forming material 11, providing both a supplemental source of cooling as well as a replenishment of water to the gel-forming resinous material. The device thereby provides cooling by evaporative cooling and by chemical reaction as well as replenishment of evaporated water to the gel-forming material, providing additional cooling for an extended time period.

Thus, the present invention provides for a simple, convenient, easily constructed, reusable device which can provide for extended cooling relief when it's user is engaged in outdoor or indoor physical activity.

While this invention has been described and illustrated herein with respect to the illustrated embodiments, it is understood that alternative embodiments and substantial equivalents are included within the scope of the invention as defined by the appended claims.

What is claimed is:

1. A device for providing evaporative cooling to a portion of the body comprising:
   a flexible, water-permeable envelope sized to contain a particulate, water-hydratable, resinous, gel-forming material; and
   an enclosure positioned in close proximity to said water-permeable envelope sized to contain reactable material for producing an endothermic or exothermic chemical reaction wherein heat may be either absorbed by or released to the immediate surroundings.

2. The device of claim 1 wherein said enclosure is impermeable and is contained within a porous membrane containing a quantity of water, said porous membrane being removably positionable within an interior space formed by the joining of two said flexible, water-permeable envelopes.

3. The device of claim 1 wherein said enclosure further comprises a waterproof, elongate, tubular enclosure having a first compartment of reactable material capable of producing either an endothermic or exothermic chemical reaction and a second compartment of fluid reactant for mixing with said reactable material, said first compartment and said second compartment being temporarily sealed from each other.

4. The device of claim 1 wherein said enclosure is impermeable and is further comprised of two separate enclosures, one containing a reactable material and one containing a fluid reactant, the chemical reaction being initiated between the reactant material and the fluid reactant by rupture of at least one of said separate enclosures.

5. The device of claim 4 wherein said separate enclosures are sealably contained within a porous membrane positioned within said flexible, water-permeable envelope, said porous membrane being filled with water.

6. The device of claim 1 wherein said reactable material is selected from a group consisting of ammonium nitrate, silver nitrate and potassium nitrate.

7. The device of claim 6 wherein said reactable material is ammonium nitrate.

8. The device of claim 1 wherein said reactable material is selected from a group consisting of calcium chloride and potassium hydroxide.

9. The device of claim 8 wherein said reactable material is calcium chloride.

10. The device of claim 1 further comprising air channels formed along an exterior surface of said flexible, water-permeable envelope.

* * * * *